United States Patent [19]

Rajadhyaksha

[11] 4,016,204

[45] Apr. 5, 1977

[54] METHOD OF SYNTHESIS OF TRANS-2-PHENYLCYCLOPROPYLAMINE

[75] Inventor: Vithal Jagannath Rajadhyaksha, Mission Viejo, Calif.

[73] Assignee: Nelson Research & Development Company, Irvine, Calif.

[22] Filed: Oct. 31, 1975

[21] Appl. No.: 627,548

[52] U.S. Cl. .................. 260/515 R; 260/570.5 CA
[51] Int. Cl.² .......................................... C07C 63/52
[58] Field of Search ................................ 260/515 R

[56] References Cited

UNITED STATES PATENTS

| 2,997,422 | 8/1961 | Tedeschi | 260/515 R X |
| 3,050,559 | 8/1962 | Burger | 260/515 R X |
| 3,153,092 | 10/1964 | Burger | 260/515 R X |

OTHER PUBLICATIONS

Burger et al., *J.A.C.S.*, 70, 2198 (1948).
Walborsky et al., *J.A.C.S.*, 83, 2138 (1961).
Burger et al., *J. Med. Pharm. Chem.*, 4, 571 (1961).
Kaiser et al., *J. Med. Pharm. Chem.*, 5, 1243 (1962).

*Primary Examiner*—James O. Thomas, Jr.
*Assistant Examiner*—G. T. Breitenstein
*Attorney, Agent, or Firm*—Martin A. Voet

[57] ABSTRACT

An improved method of synthesis of trans-2-phenylcyclopropylamine wherein the improvement comprises isomerizing an intermediate ester, namely, cis,trans-ethyl-2-phenylcyclopropanecarboxylate, by reacting said ester with anhydrous sodium ethoxide, to form a reaction product containing not more than about 5 percent cis ester and further reacting said resultant product to form trans-2-phenylcyclopropylamine.

3 Claims, No Drawings

METHOD OF SYNTHESIS OF TRANS-2-PHENYLCYCLOPROPYLAMINE

BACKGROUND OF THE INVENTION

1. Field of the Invention

The invention relates to an improved method of synthesis of trans-2-phenylcyclopropylamine.

2. Background of the Prior Art

Methods for making 2-substituted cyclopropylamines such as 2-phenylcyclopropylamine are known, e.g. Kaiser et al, Journal of Medicinal and Pharmaceutical Chemistry, 5, 1243 (1962) and U.S. Pat. No. 2,997,422. In carrying out these prior art procedures, the trans isomer of 2-phenylcyclopropylamine is prepared by reacting styrene with ethyl diazoacetate to form the ester, cis,trans-ethyl 2-phenylcyclopropanecarboxylate, and the resulting ester is hydrolyzed to the cis,trans-2-phenylcyclopropane carboxylic acid. At this stage there are 3 to 4 parts of the trans isomer to 1 part of the cis isomer. A complete separation is accomplished by repeatedly recrystallizing the acid from hot water. The pure trans isomer comes out as crystalline material while the cis isomer stays in solution. The trans-2-phenylcyclopropanecarboxylic acid is then reacted with thionyl chloride to form the acid chloride which is then successively treated with sodium azide and subjected to the Curtius degradation. The isocyanate formed by ths procedure is hydrolyzed readily to the trans-2-phenylcyclopropylamine. The foregoing process results in significant yield loss in that the cis isomer is discarded and significant amounts of trans isomer are lost in repeated recrystallizations. Furthermore, the trans isomer is contaminated by some cis isomer which results in an impure product.

Heretofore, trans-2-phenylcyclopropylamine has been used as a drug in the treatment of depression. Recently it was discovered that the (−)-enantiomer of trans-2-phenylcyclopropylamine was comparable in therapeutic effect to racemic (+)-trans 2-phenylcyclopropylamine, but had substantially fewer side effects. However, a problem related to the use of the (−)-trans isomer is that any cis impurity in the (−)-trans-2-phenylcyclopropylamine results in substantial lessening of the decrease in side effects. Therefore, it would be desirable to improve the present method of synthesis of trans-2-phenylcyclopropylamine to improve yield and purity.

SUMMARY OF THE INVENTION

There has now been discovered an improved method for improving the yield and purity of trans-2-phenylcyclopropylamine by improving the yield and purity of an intermediate, trans 2-phenylcyclopropanecarboxylic acid.

In a method for the synthesis of the intermediate trans-2-phenylcyclopropanecarboxylic acid, wherein styrene is reacted with ethyl diazoacetate to form the ester, cis,trans-ethyl-2-phenylcyclopropanecarboxylate, which ester is hydrolyzed to the acid, which acid is separated into its cis and trans isomers by repeatedly recrystalizing the trans acid from hot water to form the trans-2-phenylcyclopropanecarboxylic acid, the improvement comprising first isomerizing said cis,trans ester by refluxing said cis,trans ester with sodium ethoxide (prepared in situ by reacting sodium metal with anhydrous ethanol) to form a reaction product containing about 95% trans ester and hydrolyzing said reaction product to form the trans-2-phenylcyclopropanecarboxylic acid.

The trans 2-phenylcyclopropanecarboxylic acid is then converted by conventional reactions to the desired end product, (−)-trans-2-phenylcyclopropylamine or its pharmaceutically acceptable salts.

DETAILED DESCRIPTION OF THE INVENTION

The improved method of synthesis described herein is best illustrated by the following diagram which illustrates the conventional method of synthesis and the improved method of synthesis.

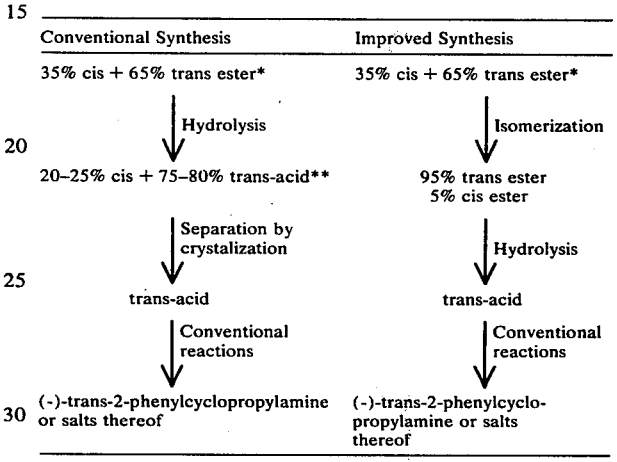

*ethyl-2-phenylcyclopropanecarboxylate
**2-phenylcyclopropanecarboxylic acid

As is apparent, a substantially increased yield of "trans-acid" results. Furthermore, the purity of the final product made by the improved method is enhanced, i.e., substantially free of cis contamination.

Optionally, the isomerization and hydrolysis reactions can be carried out in one pot. That is, after the isomerization has been achieved in the manner described herein and the trans/cis ratio confirmed, water may be added which makes the solution very basic (ethanol may be removed at this stage or before) and the solution may be hydrolyzed under reflux conditions as described herein.

More particularly, the isomerization reaction is carried out by reacting the ester, cis,trans-ethyl-2-phenylcyclopropanecarboxylate, with approximately 2N sodium ethoxide in anhydrous ethyl alcohol. Other anhydrous alkali metal alkoxides as potassium tert.-butoxide can also be used in place of sodium ethoxide. Anhydrous tert.-butanol or 1,2-dimethoxyethane can also be used in place of ethyl alcohol. The reaction generally may be carried out for about 18 to about 30 hours; and preferably for about 20 to about 24 hours; at a temperature ranging between about 70° and 80° C and preferably between about 78° and 79° C.

The following example is for purposes of illustration only. All temperatures are given in ° C.

EXAMPLE

Method of Synthesis of
(−)-trans-2-phenylcyclopropylamine sulfate.

45.6 g (0.438 M) of freshly distilled styrene in a 500 ml three-necked flask was heated to 125° under a nitrogen atmosphere. A mixture of 91.2 g (0.876 M) styrene and 100 g (0.876 M) ethyl-diazoacetate was kept at 0° and was added dropwise in portions. The addition and the temperature of the heating source was regulated in such a way that the temperature of the reaction mixture remained between 125°–140°. After the addition was complete, the reaction mixture was kept at 125° for additional 4 hours. Within this period the evolution of nitrogen had ceased. The dark red solution was then allowed to cool to room temperature overnight. Excess sytrene was removed by distillation at ~70°/50 mm. The red residual oil was distilled at 100°–105°/250 $\mu$ to obtain 122.5 g (73.5%) of a faint yellow oil. G.C. analysis (5% SE-30) showed that the mixture contained 65% trans and 35% cis isomer. Additional quantities of the reaction product were made for a total of 533 g and divided into approximately 5 batches for the following reactions.

266.5 g of sodium metal was carefully added to 5.55 l. of anhydrous ethanol under nitrogen atmosphere. The flask was cooled whenever necessary. Upon complete dissolution of metallic sodium, 533 g (2.8 M) of ($\pm$)-ethyl-2-phenylcyclopropane carboxylate (65% trans/35% cis) was added, whereupon the color of the solution changed to orange-yellow. This mixture was refluxed for 20 hours. The reaction mixture was then concentrated, the solid taken up in benzene:water and the water phase extracted with benzene. Total aqueous extracts were combined and treated as mentioned below. Total organic extracts were combined and washed with water till neutral. After drying over anhydrous soldium sulfate, the benzene solution was concentrated and yielded 299.5 g (56.19%) of isomerized ester. The combined aqueous extracts were acidified with concentrated hydrochloric acid to pH 2. The precipitated acid was filtered and dried to yield 200.7 g of ($\pm$)-trans-2-phenylcyclopropanecarboxylic acid. m.p. 93°.

To 299.5 g of isomerized ester (95% trans/5% cis) (1.574M) obtained above was added a solution of 93 g (2.3235 M) of sodium hydroxide in 863.1 ml. of absolute ethanol and 121 ml. of water. The solution was refluxed under stirring for 20 hours. Concentration of the reaction mixture gave a solid which was dissolved in water and acidified with concentrated hydrochloric acid. The precipitated solid was filtered and washed with water (cis isomer is very soluble in water and since it is less than 5% it is removed in these aqueous washings). The solid was dissolved in benzene and the organic solution was washed with water several times, dried and concentrated. The total yield of ($\pm$)-trans-2-phenylcyclopropanecarboxylic acid from 533 g of starting ester was 421.7 g (93%).

350 g (2.16 M) of ($\pm$)-trans-2-phenylcyclopropanecarboxylic acid, 312 ml. (4.34 M) of thionyl chloride and 1430 ml. of anhydrous benzene were mixed and refluxed for 16 hours. An aliquot was concentrated and analyzed on G.C. by converting it to its methyl ester with methanol. It showed more than 99% of trans acid chloride. The dark reaction mixture was concentrated and the residue was distilled at ~100°/1 mm. to give 369 g. (95%) of light yellow product.

A three-necked flask (2liter) equipped with a dropping funnel, a condenser and a mechanical stirrer was charged with 112.5 g. (1.73 M) of sodium azide and 375 ml. of toluene. This suspension was heated to 80° and a solution of 75 g. (0.415 M) of ($\pm$)-trans-2-phenylcyclopropane carboxylic acid chloride in 350 ml. of dry toluene was added dropwise over 1½ hour period. During the addition, the temperature was maintained at 80° and there was a slow evolution of nitrogen. After the addition was over, the reaction mixture was refluxed for 3–4 hours and by this time the evolution of nitrogen had subsided. The mixture was then allowed to cool overnight, filtered and the solid residue was washed several times with dry benzene or dry toluene. The combined organic solution was concentrated at reduced pressure to an oil. This isocyanate intermediate was not purified and was used directly in the next step.

The oil was cooled in an ice-bath and 600 ml. of concentrated hydrochloric acid (37%) was added in 2–3 portions carefully. Vigorous evolution of carbon dioxide gas was noted. After this evolution had subsided, the reaction mixture was refluxed for 15 hours, cooled and extracted three times with 300 ml. each of ether. The aqueous phase was concentrated under reduced pressure and the residual tan solid was dissolved in a minimum amount of water. This solution was cooled in an ice-bath and made strongly basic with 60% potassium hydroxide and extracted with methylene chloride several times. The methylene chloride solution was dried, concentrated to an oil at reduced pressure and the oil was distilled at 70°–75°/500$\mu$ to obtain 46.9 g. (85%) of colorless ($\pm$)-trans-2-phenylcyclopropylamine.

688.55 g. (4.58758 M) of ($\pm$)-tartaric acid was dissolved in 3400 ml. of absolute ethanol. The solution was cooled in an ice-bath and stirred vigorously. 611 g. (4.58743 M) of ($\pm$)-trans-2-phenylcyclopropylamine was added as an oil. 75 ml of absolute ethanol was used to rinse the residual amine in the flask and this was added to the main portion immediately. The reaction was exothermic and very soon the diastereomeric salts precipitated out. The mixture was cooled and filtered to yield 1280 g. (98.5%) of diastereomeric tartrates. After drying under high vacuum, the white powder was recrystallized four times from isopropanol/water (75:25) to give white crystals. The technique followed was to get as concentrated a solution as possible while maintaining a clear solution at 70°–75° C. The solution was allowed to cool slowly at room temperature and then just before filtration was cooled in an ice-bath. Generally, four or five crystallizations were necessary to get complete resolution which was indicated by the appropriate melting point and specific rotation of the salt. Yield of the (−)-Amine (+)-tartrate was 360 g. (56.25%), m.p. 189°–191°. Specific rotation $[\alpha]_D^{25} = -30.1°$ (C=0.0353 M, 1%, Water).

360 g. of the salt obtained above was made basic to pH 12 with 60% KOH and the cloudy solution was extracted with ether. The combined ether extracts were washed with water, dried and concentrated. Yield of the free amine was 153.2 g. (91%).

The clear oil was dissolved in absolute ethanol and to this cooled solution was added an ethanolic solution of concentrated sulphuric acid till the pH was about 3. The solid was filtered, washed with ethanol and dried. Yield: 135 g. (65%). The lower yield was due to solubility of the product in ethanol. Melting point: 242°–243° C, Specific rotation: of the (−)-trans-2-phenylcyclopropylamine sulfate was $[\alpha]_D^{25} = -70.5°$, (C=0.0549 M, 1%, Water).

I claim:

1. In a method for the synthesis of trans-2-phenylcyclopropanecarboxylic acid, wherein styrene is reacted with ethyl diazoacetate to form the ester, cis,trans-ethyl-2-phenylcyclopropanecarboxylate, which ester is hydrolyzed to form the corresponding acid, cis,trans-2-phenylcyclopropanecarboxylic acid, from which the trans isomer, trans-2-phenylcyclopropanecarboxylic acid is obtained by repeated crystallizations, the improvement comprising first isomerizing said cis,trans ester to form a reaction product containing about 95% trans ester by reacting said ester with an anhydrous alkali metal alkoxide in an anhydrous alcohol and hydrolyzing said reaction product to form the trans-2-phenylcyclopropanecarboxylic acid.

2. The method of claim 1 wherein said isomerization is carried out by reacting said cis,trans ester with sodium ethoxide in anhydrous ethanol at a temperature ranging between about 70° and 80° C for about 18 to about 30 hours.

3. The method of claim 1 wherein the anhydrous alcohol is selected from the group consisting of ethanol, tertiary butanol and 1,2-dimethoxyethanol.

* * * * *